US00PP14807P2

(12) United States Plant Patent
Boeder

(10) Patent No.: US PP14,807 P2
(45) Date of Patent: May 18, 2004

(54) CHRYSANTHEMUM PLANT NAMED 'ARTIST PINK'

(50) Latin Name: *Chrysanthemum morifolium L.*
Varietal Denomination: Artist Pink

(75) Inventor: Mark Roland Boeder, The Hague (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 10/426,844

(22) Filed: May 1, 2003

(51) Int. Cl.[7] ..... A01H 5/00
(52) U.S. Cl. ..... Plt./286
(58) Field of Search ..... Plt./286

*Primary Examiner*—Anne Marie Grunberg
*Assistant Examiner*—Annette H. Para
(74) *Attorney, Agent, or Firm*—Parkhurst & Wendel, L.L.P.

(57) ABSTRACT

A Chrysanthemum plant named 'Artist Pink' characterized by its medium sized blooms with white/pink ray-florets and green disc florets.

3 Drawing Sheets

RELATED CULTIVARS

'Artist Pink' is related to 'Artist Yellow' (copending U.S. Plant patent application Ser. No. 10/426,861) as both plants are developed from similar breeding programmes.

BACKGROUND OF THE INVENTION

'Artist Pink' is a product of a breeding-program which had the objective of creating new chrysanthemum cultivars with a daisy type flower, a 7–8 week response and a medium plant height (90 cm). The new plant of the present invention comprises a new and distinct cultivar of Chrysanthemum plant. 'Artist Pink' is a seedling from a cross in a breeding program maintained under the control of inventor. The female parent is an unnamed seedling not available to inventor for description. The male is unknown, being a mixed population of a group of male parents. The new and distinct cultivar was discovered and selected as a flowering plant within the progeny of the stated cross by Mark Boeder in a controlled environment (greenhouse) in Rijsenhout Holland in 2001. The first act of asexual reproduction of 'Artist Pink' was accomplished when vegeatative cuttings were taken from the initial selection in 2001 in a controlled environment in Rijsenhout Holland.

SUMMARY OF THE INVENTION

The present invention is a new and distinct variety of chrysanthemum bearing medium sized blooms with white/pink ray-florets and green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
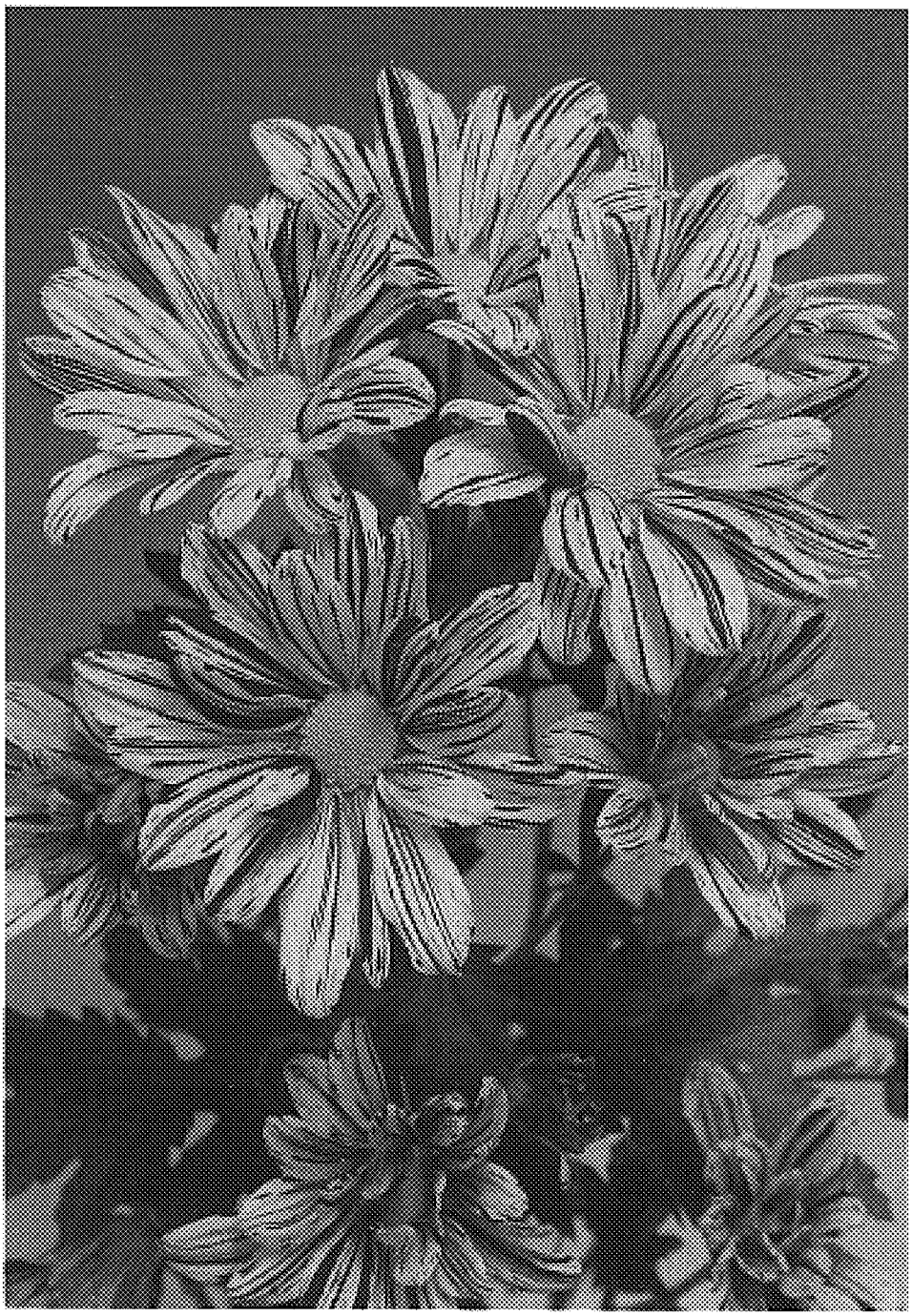
FIG. 1 shows a plant of the cultivar in full bloom.
Figure 2:
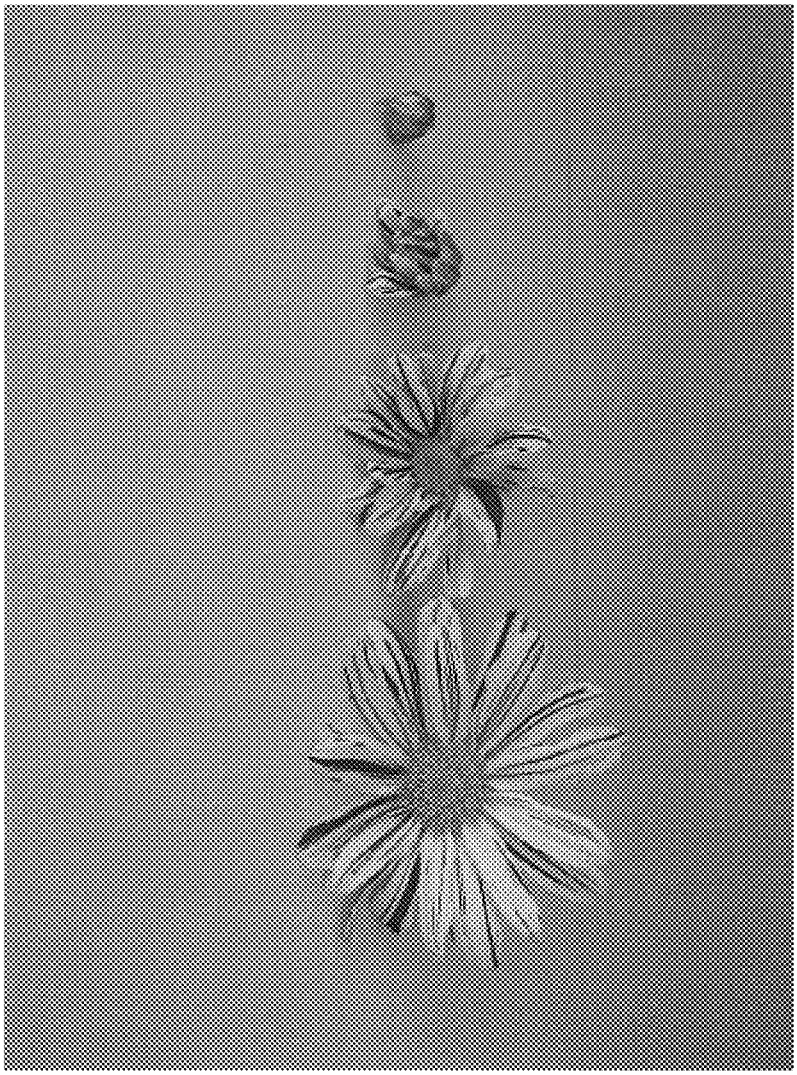
FIG. 2 shows the various stages of bloom of the new cultivar.
Figure 3:
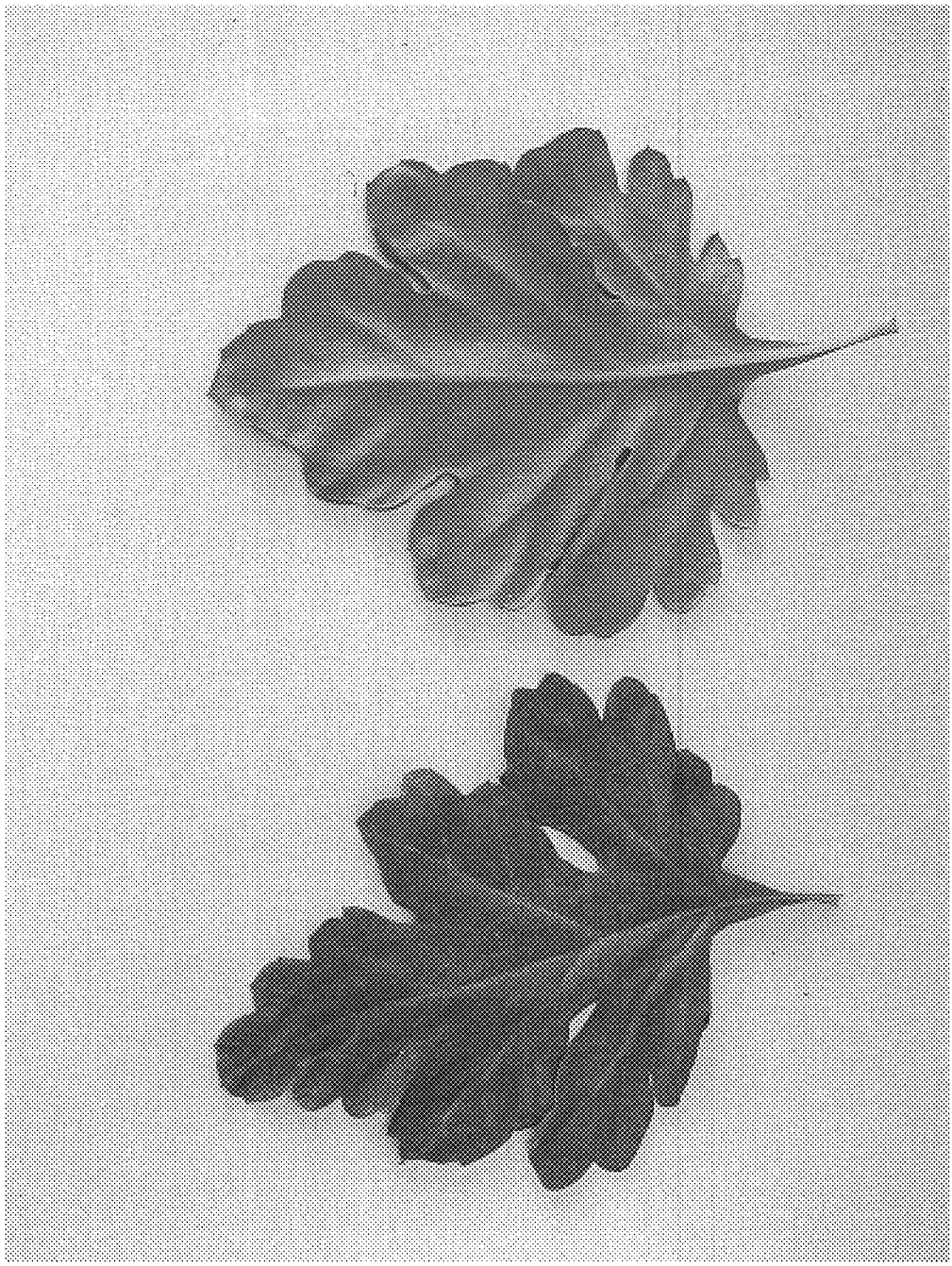
FIG. 3 shows the foliage of the new cultivar.

This new variety of chrysanthemum is of the botanical classification *Chrysanthemum morifolium* L. The observations and measurements were gathered from plants grown in April/May in a greenhouse in Rijsenhout Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 52 days. After the long day period to flowering plant growth retardants were applied 3 times in a dose of 2 gram/liter water. The plants were observed (directly) during the flowering of this crop. The plant is resistant to infestation by Powdery Mildew. No tests were done on cold or drought tolerance. This new variety produces medium sized blooms with white/pink ray-florets and green dis-florets blooming on the plant for 4 weeks. This new variety of chrysanthemum has been found to retain its distinctive characteristics throughout successive propagations however the phenotype may vary significantly with variations in environment such as light intensity and temperature. To show the phenotype as described 'Artist Pink' can be planted without assimilation lightning (high pressure sodium lamps) between week 1 and week 52 of the next year under greenhouse conditions in Holland. With assimilation light (minimum level 2500 lux) it can be planted year round under greenhouse conditions in Holland.

From the cultivars known to inventor the most similar existing cultivar in comparison to 'Artist Pink' is 'Artist Yellow' (copending U.S. Plant patent application Ser. No. 10/426,861). When 'Artist Yellow' and 'Artist Pink' are being compared the following differences and similarities are noticed: Both plants are novel types of bicolored chrysanthemum plants, with ray-florets having contrasting colored streaks along the longitudinal axis. The differences of 'Artist Yellow' and 'Artist Pink' are (1) Bloom color (2) and Spray shape. (1) Bloom color—The color of ray-florets of 'Artist Yellow' is yellow/orange while that of 'Artist Pink' is white/pink. (2) Spray shape—The shape of 'Artist Yellow' is cylindrical, while that of 'Artist Pink' is corymbiform.

The following is a description of the plant and characteristics that distinguish 'Artist Pink' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical description of cultivar 'Artist Pink':

Bud:

*Size.*—Medium, cross-section 0.9 cm height 1 cm.
*Outside color.*—White 155 A.
*Involucral bracts.*—2 rows, length 7 mm, width 3 mm.
*Involucral bracts among disc-florets.*—Not present.
*Involucral bracts color.*—Green 138 C.

Bloom:

*Type.*—Daisy.
*Size.*—Medium.
*Fully expanded.*—6.5–7 cm.
*Number of blooms per stem.*—Average of 20.
*Performance on the plant.*—4 weeks.
*Seeds* (*if crossed*).—Produced in small quantities, oval shaped, grey-brown 199A, 2 mm in length.
*Fragrance.*—Typical chrysanthemum, slight.
*Peduncle length.*—Near the top 8 cm, near the middle 9 cm, near the bottom 10 cm.
*Peduncle color.*—Green 137 C.

Color:

*Center of the flower* (*disc-florets*).—Immature Yellow-green 144 A. Mature Yellow-orange 15A.
*Color of the ray-florets.*—Upper surface White 155 D with streaks of Greyed-purple 186 A. Lower surface White 155 with Greyed-purple 186 C.
*Tonality from distance.*—A spray mum with white/pink flowers and green disc.
*Color of the upper surface of the ray-florets after aging of the plant.*—White 155 D with streaks of Greyed-purple 186 A.

Ray florets:

*Texture.*—Upper and under side smooth.
*Number.*—20.
*Cross-section.*—Concave.
*Longitudinal axis of majority.*—Straight.
*Length of corolla tube.*—0.5 cm.
*Ray-floret margin.*—Entire.
*Ray-floret length.*—3–3.5 cm.
*Ray-floret width.*—1 cm.
*Ratio length/width.*—Medium.
*Shape of tip.*—Rounded.

Disc florets:

*Disc diameter.*—1.3–1.5 cm.
*Distribution of disc florets.*—Numerous, clearly visible at all stages of flowering.
*Shape.*—Tubular.
*Receptacle shape.*—Domed Raised.

Reproductive organs:

*Stamen* (*present in disc florets only*).—Thin 3 mm in length.
*Stamen color.*—Yellow-green 144 B.
*Pollen.*—Present.
*Pollen color.*—Yellow-orange 14 A.
*Styles* (*present in both ray and disc florets*).—Thin.
*Style color.*—Yellow-green 144 B.
*Style length.*—0.6 cm.
*Stigma color.*—Yellow-green 144 B.
*Stigma width.*—0.2 cm.
*Ovaries.*—Enclosed in florets.

Plant:

*Form.*—A spray mum meant for erect culture.
*Growth habit.*—Upright.
*Growth rate.*—Vigorous.
*Height.*—90 cm.
*Width.*—25 cm.
*Internode lenght.*—3–4 cm.
*Spray formation.*—Corymbiform.
*Stem color.*—Green 137 C.
*Stem strength.*—Strong.
*Stem brittleness.*—Not brittle.
*Stem anthocyanin coloration.*—Absent.
*Flowering response* (*photo-periodic controlled crop, not natural season*).—52 days.

Foliage:

*Color immature stage.*—Upper side Green 137 B. Under side Green 137 C.
*Color mature stage.*—Upper side Green 137 A. Under side Green 137 B.
*Color midvein mature leaf.*—Upper side Yellow-green 145 C. Under side Yellow-green 145 C.
*Size.*—Medium; length 11 cm, width 5 cm.
*Quantity* (*number per single stem*).—18–20.
*Shape.*—Cordiform.
*Texture upper side.*—Fleshy and glabrous.
*Texture under side.*—Pubescent.
*Venation arrangement.*—Palmate.
*Shape of the margin.*—Dentate.
*Shape of base of sinus between lateral lobes.*—Diverging.
*Margin of sinus between lateral lobes.*—Rounded.
*Shape of base.*—Rounded.
*Apex.*—Mucronulate.
*Petiole lenght.*—2 cm.
*Petiole color.*—Yellow-green 145 C.

Differences with the comparison Varieties

| | 'Artist Pink' | 'Artist Yellow' |
|---|---|---|
| Color of the upper side of the ray-florets | White 155 D and Greyed-purple 186 B | Yellow-orange 14 B and Red 46 A |
| Spray form | Corymbiform | Cylindrical |

I claim:

1. A new and distinct variety of chrysanthemum plant as described and illustrated.

* * * * *